(12) United States Patent
Blank et al.

(10) Patent No.: US 6,512,937 B2
(45) Date of Patent: Jan. 28, 2003

(54) MULTI-TIER METHOD OF DEVELOPING LOCALIZED CALIBRATION MODELS FOR NON-INVASIVE BLOOD ANALYTE PREDICTION

(75) Inventors: Thomas B. Blank, Chandler, AZ (US); Stephen L. Monfre, Gilbert, AZ (US); Timothy L. Ruchti, Gilbert, AZ (US); Suresh Thennadil, Tempe, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 0 days.

(21) Appl. No.: 09/825,687

(22) Filed: Apr. 3, 2001

(65) Prior Publication Data

US 2001/0021803 A1 Sep. 13, 2001

Related U.S. Application Data

(63) Continuation-in-part of application No. 09/359,191, filed on Jul. 22, 1999, now Pat. No. 6,280,381.

(51) Int. Cl.[7] .................................................. A61B 5/00
(52) U.S. Cl. ........................................ 600/322; 128/920
(58) Field of Search ................................. 600/310, 322, 600/323, 330, 336, 473; 128/920, 923, 924, 925; 356/402; 250/340, 341.1, 339.01

(56) References Cited

U.S. PATENT DOCUMENTS 5,553,616 A * 9/1996 Ham et al. .................. 128/925
5,576,544 A * 11/1996 Rosenthal ................. 250/341.1
5,725,480 A * 3/1998 Oosta et al. ................. 600/310
5,798,526 A * 8/1998 Shenk et al. ........... 250/339.09

* cited by examiner

Primary Examiner—Eric F. Winakur
(74) Attorney, Agent, or Firm—Michael A. Glenn; Chris Peil

(57) ABSTRACT

A method of multi-tier classification and calibration in noninvasive blood analyte prediction minimizes prediction error by limiting co-varying spectral interferents. Tissue samples are categorized based on subject demographic and instrumental skin measurements, including in vivo near-IR spectral measurements. A multi-tier intelligent pattern classification sequence organizes spectral data into clusters having a high degree of internal consistency in tissue properties. In each tier, categories are successively refined using subject demographics, spectral measurement information and other device measurements suitable for developing tissue classifications.

The multi-tier classification approach to calibration utilizes multivariate statistical arguments and multi-tiered classification using spectral features. Variables used in the multi-tiered classification can be skin surface hydration, skin surface temperature, tissue volume hydration, and an assessment of relative optical thickness of the dermis by the near-IR fat band. All tissue parameters are evaluated using the NIR spectrum signal along key wavelength segments.

23 Claims, 9 Drawing Sheets

MULTI-TIER METHOD OF DEVELOPING LOCALIZED CALIBRATION MODELS FOR NON-INVASIVE BLOOD ANALYTE PREDICTION

CROSS-REFERENCE TO RELATED APPLICATION

This application is a Continuation-in-part of U.S. patent application Ser. No. 09/359,191; filed on Jul. 22, 1999, now U.S. Pat. No. 6,280,381.

BACKGROUND OF THE INVENTION

1. Field of the Invention

The invention relates to non-invasive blood analyte predication using near IR tissue absorption spectra. More particularly, the invention relates to a method of classifying sample spectra into groups having a high degree of internal consistency to minimized prediction error due to spectral interferents.

2. Description of Related Technology

The goal of noninvasive blood analyte measurement is to determine the concentration of targeted blood analytes without penetrating the skin. Near infrared (NIR) spectroscopy is a promising noninvasive technology that bases measurements on the absorbance of low energy NIR light transmitted into a subject. The light is focused onto a small area of the skin and propagates through subcutaneous tissue. The reflected or transmitted light that escapes and is detected by a spectrometer provides information about the contents of the tissue that the NIR light has penetrated and sampled. The absorption of light at each wavelength is determined by the structural properties and chemical composition of the tissue. Tissue layers, each containing a unique heterogeneous chemistry and particulate distribution, result in light absorption and scattering of the incident radiation. Chemical components such as water, protein, fat and blood analytes absorb light proportionally to their concentration through unique absorption profiles. The sample tissue spectrum contains information about the targeted analyte, as well as a large number of other substances that interfere with the measurement of the analyte. Consequently, analysis of the analyte signal requires the development of a mathematical model for extraction of analyte spectral signal from the heavily overlapped spectral signatures of interfering substances. Defining a model that produces accurate compensation for numerous interferents may require spectral measurements at one hundred or more frequencies for a sizeable number of tissue samples.

In equation 7, T is a matrix representing the concentration or magnitude of interferents in all samples, and P represents the pure spectra of the interfering substances or effects present. Any spectral distortion can be considered an interferent in this formulation. For example, the effects of variable sample scattering and deviations in optical sampling volume must be included as sources of interference in this formulation. The direct calibration for a generalized least squares model on analyte y is $$y_{GLS}=(K^T\_^{-1}K)^{-1}K^T\_^{-1}(x-k_0) \qquad (8)$$

where _ is defined as the covariance matrix of the interfering substances or spectral effects, $\hat{U}$ is defined as the measurement noise, x is the spectral measurement, and $k_0$ is the instrument baseline component present in the spectral measurement.

Accurate noninvasive estimation of blood analytes is also limited by the dynamic nature of the sample, the skin and living tissue of the patient. Chemical, structural and physiological variations occur produce dramatic changes in the optical properties of the measured tissue sample. See R. Anderson, J. Parrish. The optics of human skin, *Journal of Investigative Dermatology*, vol. 77(1), pp. 13–19 (1981); and W. Cheong, S. Prahl, A. Welch, A review of the optical properties of biological tissues, *IEEE Journal of Quantum Electronics*, vol. 26(12), pp. 2166–2185 (December 1990); and D. Benaron, D. Ho, Imaging (NIRI) and quantitation (NIRS) in tissue using time-resolved spectrophotometry: the impact of statically and dynamically variable optical path lengths, *SPIE*, vol. 1888, pp.10–21 (1993); and J. Conway, K. Norris, C. Bodwell, A new approach for the estimation of body composition: infrared interactance, *The American Journal of Clinical Nutrition*, vol. 40, pp. 1123–1140 (December 1984); and S. Homma, T. Fukunaga, A. Kagaya, Influence of adipose tissue thickness in near infrared spectroscopic signals in the measurement of human muscle, *Journal of Biomedical Optics*, vol. 1(4), pp. 418–424 (October 1996); and A. Profio, Light transport in tissue, *Applied Optics*, vol. 28(12), pp. 2216–2222 (June 1989); and M. Van Gemert, S. Jacques, H. Sterenborg, W. Sta, Skin optics, *IEEE Transactions on Biomedical Engineering*, vol. 36(12), pp. 1146–1154 (December 1989); and B. Wilson, S. Jacques, Optical reflectance and transmittance of tissues: principles and applications, *IEEE Journal of Quantum Electronics*, vol. 26(12), pp. 2186–2199.

Overall sources of spectral variations include the following general categories:

1. Co-variation of spectrally interfering species. The near infrared spectral absorption profiles of blood analytes tend to overlap and vary simultaneously over brief time periods. This overlap leads to spectral interference and necessitates the measurement of absorbance at more independently varying wavelengths than the number of interfering species.

2. Sample heterogeneity. The tissue measurement site has multiple layers and compartments of varied composition and scattering. The spectral absorbance versus wavelength measurement is related to a complex combination of the optical properties and composition of these tissue components. Therefore, the spectral response with changing blood analyte concentration is likely to deviate from a simple linear model.

3. State Variations. Variations in the subject's physiological state effect the optical properties of tissue layers and compartments over a relatively short period of time. Such variations, for example, may be related to hydration levels, changes in the volume fraction of blood in the tissue, hormonal stimulation, skin temperature fluctuations and blood hemoglobin levels. Subtle variations may even be expected in response to contact with an optical probe.

4. Structural Variations. The tissue characteristics of individuals differ as a result of factors that include hereditary, environmental influences, the aging process, sex and body composition. These differences are largely anatomical and can be described as slowly varying structural properties producing diverse tissue geometry. Consequently, the tissue of a given subject may have distinct systematic spectral absorbance features or patterns that can be related directly to specific characteristics such as dermal thickness, protein levels and percent body fat. While the absorbance features may be repeatable within a patient, the structural variations in a population of patients may not be amenable to the use of a single mathematical calibration model.

Therefore, differences between patients are a significant obstacle to the noninvasive measurement of blood analytes through NIR spectral absorbance.

In a non-dispersive system, variations similar to (1) above are easily modeled through multivariate techniques such as multiple linear regression and factor-based algorithms. Significant effort has been expended to model the scattering properties of tissue in diffuse reflectance, although the problem outlined in (2) above has been largely unexplored. Variation of the type listed in (3) and (4) above causes significant nonlinear spectral response for which an effective solution has not been reported. For example, several reported methods of noninvasive glucose measurement develop calibration models that are specific to an individual over a short period of time. See K. Hazen, Glucose determination in biological matrices using near-infrared spectroscopy, Doctoral Dissertation, University of Iowa (August 1995); and J. Burmeister, In vitro model for human noninvasive blood glucose measurements, Doctoral Dissertation, University of Iowa (December 1997); and M. Robinson, R. Eaton, D. Haaland, G. Koepp, E. Thomas, B. Stallard and P. Robinson, Noninvasive glucose monitoring in diabetic patients: a preliminary evaluation, *Clin. Chem*, vol. 38 (9), pp. 1618–1622 (1992). This approach avoids modeling the differences between patients and therefore cannot be generalized to more individuals. However, the calibration models have not been tested over long time periods during which variation of type (4) may require recalibration. Furthermore, the reported methods have not been shown to be effective over a range of type (3) variations.

SUMMARY OF THE INVENTION

The invention provides a Multi-Tier method for classifying tissue absorbance spectra that localizes calibration and sample spectra into local groups that are used to reduce variation in sample spectra due to co-variation of spectral interferents, sample heterogeneity, state variation and structural variation. Measurement spectra are associated with localized calibration models that are designed to produce the most accurate estimates for the patient at the time of measurement. Classification occurs through extracted features of the tissue absorbance spectrum related to the current patient state and structure.

The invention also provides a method of developing localized calibration models from tissue absorbance spectra from a representative population of patients or physiological states of individual patients that have been segregated into groups. The groups or classes are defined on the basis of structural and state similarity such that the variation in tissue characteristics within a class is smaller than the variation between classes.

DETAILED DESCRIPTION
MULTI-TIERED CLASSIFICATION

The classification of tissue samples using spectra and other electronic and demographic information can be approached using a wide variety of algorithms. A wide range of classifiers exists for separating tissue states into groups having high internal similarity: for example, Bayesian classifiers utilizing statistical distribution information; or nonparametric neural network classifiers that assume little a priori information. See K. Funkunaga, *Intro to Statistical Pattern Recognition*, Academic Pres, San Diego, Calif. (1990); and J. Hertz, A. Krogh, R. Palmer, *Introduction To The Theory Of Neural Computation*, Addison-Wesley Publishing Co., Redwood City, Calif. (1991). The multi-tiered classification approach selected here provides the opportunity to grow and expand the classification database as more data become available. The multi-tiered classifier is similar to a hierarchic classification tree, but unlike a classification tree, the decision rules can be defined by crisp or fuzzy functions and the classification algorithm used to define the decision rule can vary throughout the tree structure.

Figure 1:
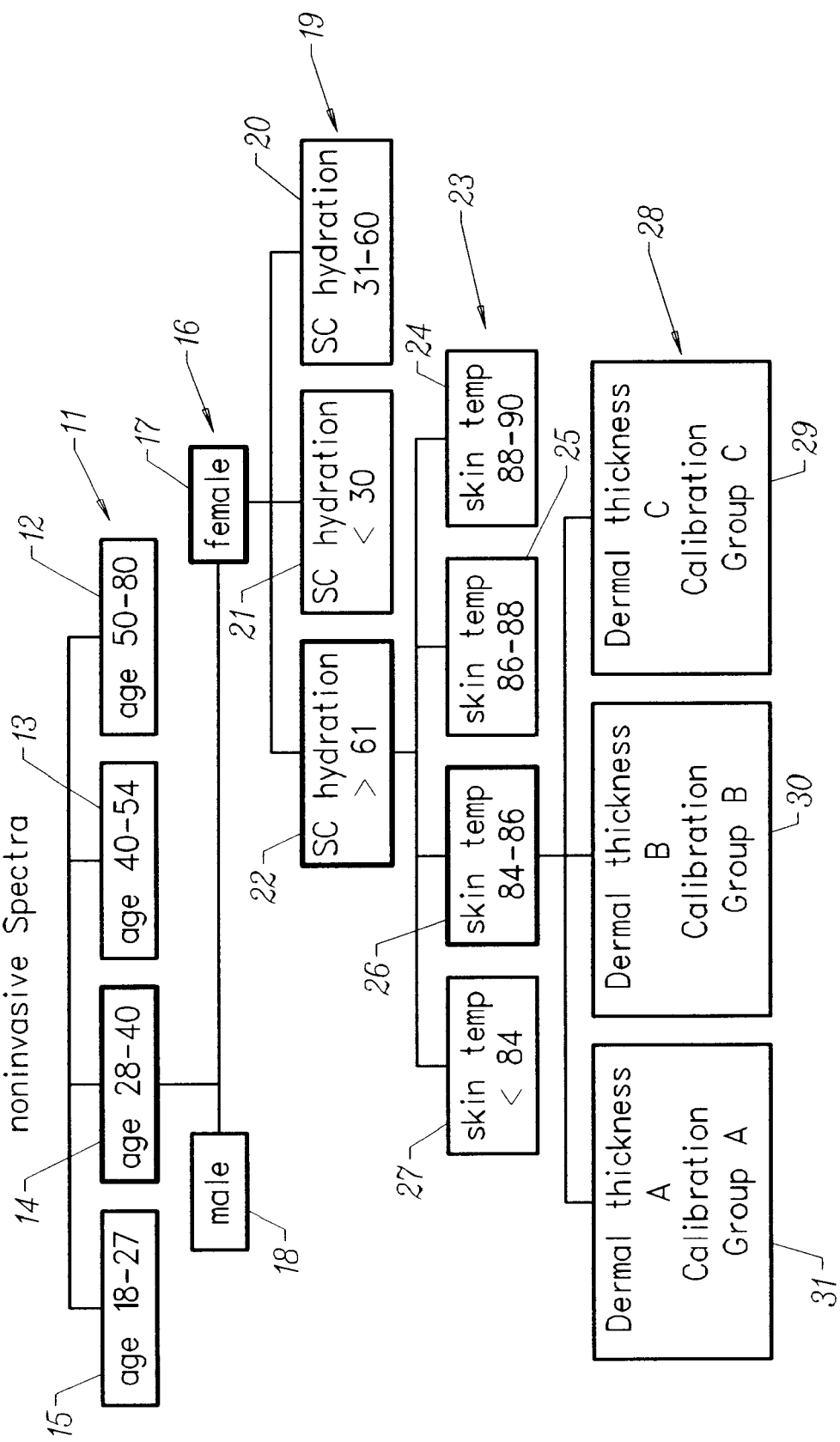
FIG. 1 provides a representation of a Multi-Tiered Classification Tree structure, according to the invention.

Referring now to FIG. 1, an example of a Multi-Tiered Classification scheme is represented. A first tier 11 assigns sample spectra according to pre-defined age groups: 18–27 (15), 28–40 (14), 40–54 (13) and 55–80 years old (12). As indicated, a sample has been assigned to the 28–40 age group. A second tier 16 assigns samples to classes 18, 17 according to sex, in this case female. A third tier 19, groups according to stratum corneum hydration: 31–60 (20); <30 (21) and >61 corneometer units (22); in this case, >61. A fourth tier 23, groups according to skin temperature: 88–90 (24); 86–88 (25); 84–86 and <84 degrees; in this case 84–86 degrees. In this way, a determination of class membership is made within each tier in the multi-tiered structure. Finally, in a last tier 28, a final class assignment is made into one of three pre-defined groups 29, 30 and 31 according to relative optical thickness of the dermis.

For economy's sake, only the branching adjacent the selected classes is completely shown in FIG. 1, though there would be many more intermediate and final classification categories in a full multi-tiered classification structure. For example, at the fourth tier 23 of Figure, there would be ninety-six possible classifications for a tissue measurement spectrum; at the final tier, there would be two hundred eighty-eight possible classifications. The foregoing description of a Multi-Tier Classification structure is meant to be exemplary only. One skilled in the art will appreciate that an actual classification structure could have more or fewer tiers, and different decision rules could be utilized at each tier than have been utilized in the example.

FEATURE EXTRACTION

As previously indicated, at each tier in the classification structure, classification is made based on a priori knowledge of the sample, or on the basis of instrumental measurements made at the tissue measurement site. In the example of FIG. 1, the first two tiers utilize a priori information about the sample: subject age and sex. Successive tiers utilize information gained from instrumental measurements at the tissue measurement site. Further classification occurs on the basis of extracted features from the tissue absorbance spectra themselves.

Figure 2:
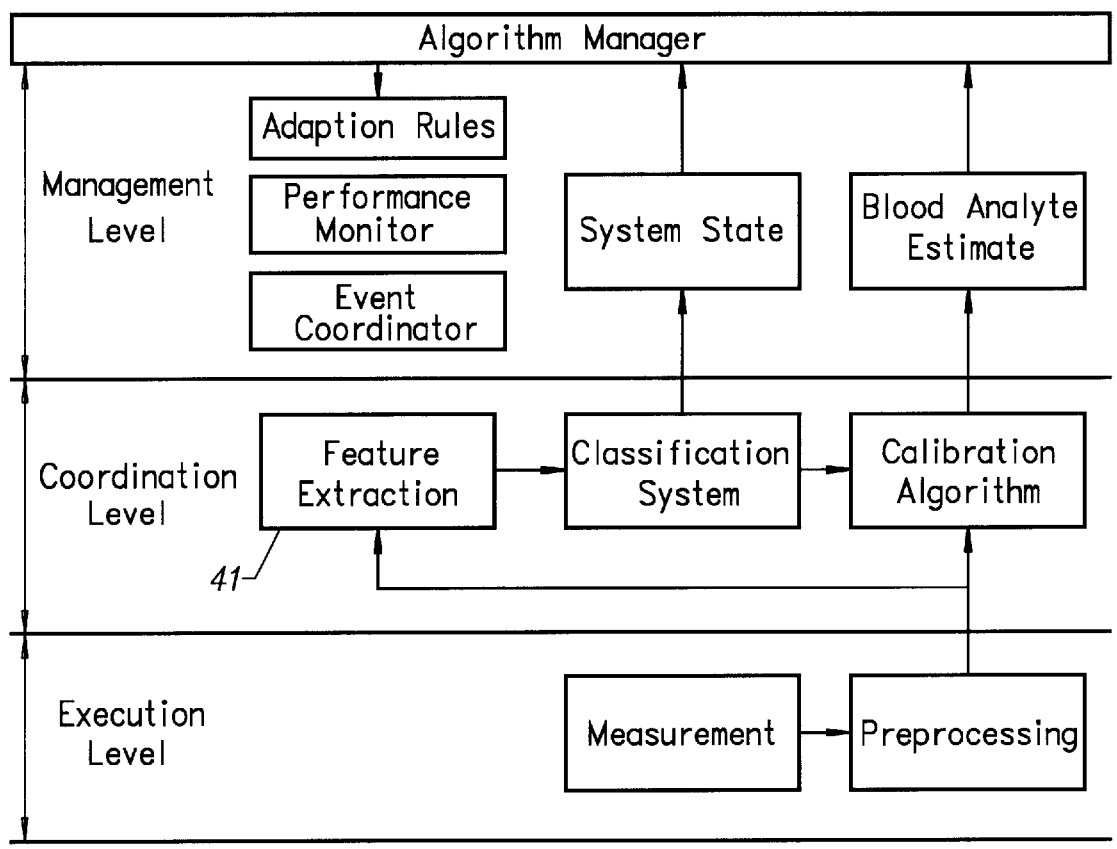
FIG. 2 is a block diagram of the architecture of an intelligent system for the noninvasive measurement of blood analytes, according to the invention.

Feature extraction is any mathematical transformation that enhances a quality or aspect of the sample measurement for interpretation. See R. Duda, P. Hart, *Pattern Classification and Scene Analysis*, John Wiley and Sons, New York (1973). FIG. 2 shows a block diagram of an intelligent measurement system for noninvasive blood analyte prediction, fully described in the parent application to the current application: S. Malin and T. Ruchti, An Intelligent System For Noninvasive Blood Analyte Prediction, U.S. patent application Ser. No. 09/359,191; Jul. 22, 1999, The purpose of feature extraction 41 in FIG. 2 is to concisely represent the structural properties and physiological state of the tissue measurement site. The set of features is used to classify the patient and determine the calibration model(s) most useful for blood analyte prediction.

The features are represented in a vector, $z \in \Re^M$ that is determined from the preprocessed measurement through $$z = f(\lambda, x) \quad (1)$$

where f: $\Re^N \to R^M$ is a mapping from the measurement space to the feature space. Decomposing f(•) will yield specific transformations, $f_i(•)$: $\Re^N \to \Re^{M_i}$ for determining a specific feature. The dimension, $M_i$, indicates whether the $i^{th}$ feature is a scalar or a vector and the aggregation of all features is the vector z. When a feature is represented as a vector or a pattern, it exhibits a certain structure indicative of an underlying physical phenomenon.

The individual features are divided into two categories:

1. abstract and
2. simple.

Abstract features do not necessarily have a specific interpretation related to the physical system. Specifically, the scores of a principal component analysis are useful features although their physical interpretation is not always known. The utility of the principal component analysis is related to the nature of the tissue absorbance spectrum. The most significant variation in the tissue spectral absorbance is not caused by a blood analyte but is related to the state, structure and composition of the measurement site. This variation is modeled by the primary principal components. Therefore, the leading principal components tend to represent variation related to the structural properties and physiological state of the tissue measurement site. Simple features are derived from an a priori understanding of the sample and can be related directly to a physical phenomenon. Useful features that can be calculated from NIR spectral absorbance measurements include but are not limited to:

1. Thickness of adipose tissue. See J. Conway, K. Norris, C. Bodwell, A new approach for the estimation of body composition: infrared interactance, *The American Journal of Clinical Nutrition*, vol. 40, pp. 1123–1140 (December 1984) and S. Homma, T. Fukunaga, A. Kagaya, Influence of adipose tissue thickness in near infrared spectroscopic signals in the measurement of human muscle, *Journal of Biomedical Optics*, vol.1(4), pp. 418–424 (October 1996).
2. Tissue hydration. See K. Martin, Direct measurement of moisture in skin by NIR spectroscopy, *J. Soc. Cosmet. Chem.*, vol. 44, pp. 249–261 (September/October 1993).
3. Magnitude of protein absorbance. See J. Conway, et al., supra.
4. Scattering properties of the tissue. See A. Profio, Light transport in tissue, *Applied Optics*, vol. 28(12), pp. 2216–2222 (June 1989) and W. Cheong, S. Prahl, A. Welch, A review of the optical properties of biological tissues, *IEEE Journal of Quantum Electronics*, vol. 26(12), pp. 2166–2185 (December 1990); and R. Anderson, J. Parrish. The optics of human skin, *Journal of Investigative Dermatology*, vol. 77(1), pp. 13–19 (1981).
5. Skin thickness. See Anderson, et al., supra; and Van Gemmert, et al., supra.
6. Temperature related effects. See Funkunga, supra.
7. Age related effects. See W. Andrew, R. Behnke, T. Sato, Changes with advancing age in the cell population of human dermis, *Gerontologia*, vol. 10, pp. 1–19 (1964/65); and W. Montagna, K. Carlisle, Structural changes in aging human skin, *The Journal of Investigative Dermatology*, vol. 73, pp. 47–53 (1979; and 19 J. Brocklehurst, *Textbook of Geriatric Medicine and Gerontology*, pp.593–623, Churchill Livingstone, Edinburgh and London (1973).
8. Spectral characteristics related to sex. See T. Ruchti, Internal Reports and Presentations, Instrumentation Metrics, Inc.
9. Pathlength estimates. See R. Anderson, et al., supra and S. Matcher, M. Cope, D. Delpy, Use of water absorption spectrum to quantify tissue chromophore concentration changes in near-infrared spectroscopy, *Phys. Med. Biol.*, vol. 38, pp. 177–196 (1993).
10. Volume fraction of blood in tissue. See Wilson, et al., supra.
11. Spectral characteristics related to environmental influences.

Spectral decomposition is employed to determine the features related to a known spectral absorbance pattern. Protein and fat, for example, have known absorbance signatures that can be used to determine their contribution to the tissue spectral absorbance. The measured contribution is used as a feature and represents the underlying variable through a single value.

Features related to demographic information, such as age, are combinations of many different effects that cannot be represented by a single absorbance profile. Furthermore, the relationship of demographic variables and the tissue spectral absorbance is not deterministic. For example, dermal thickness and many other tissue properties are statistically related to age but also vary substantially as a result of hereditary and environmental influences. Therefore, factor based methods are employed to build models capable of representing variation in the measured absorbance related to the demographic variable. The projection of a measured absorbance spectrum onto the model constitutes a feature that represents the spectral variation related to the demographic variable. The compilation of the abstract and simple features constitutes the M-dimensional feature space. Due to redundancy of information across the set of features, optimum feature selection and/or data compression is applied to enhance the robustness of the classifier.

CLASSIFICATION

The goal of feature extraction is to define the salient characteristics of measurements that are relevant for classification. Feature extraction is performed at branching junctions of the multi-tiered classification tree structure. The goal of the classification step is to assign the calibration model(s) most appropriate for a particular noninvasive measurement. In this step the patient is assigned to one of many predefined classes for which a calibration model has been developed and tested. Since the applied calibration model is developed for similar tissue absorbance spectra, the blood analyte predictions are more accurate than those obtained from a universal calibration model.

Figure 3:
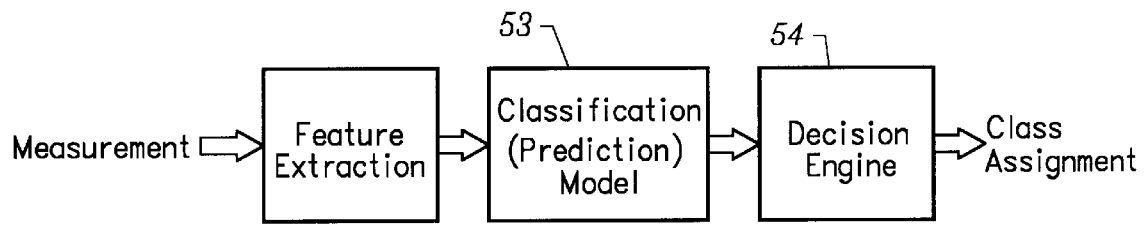
FIG. 3 is a block diagram of a pattern classification system, according to the invention.

As depicted in FIG. 3, pattern classification generally involves two steps:

1. a mapping step in which a classification model 53 measures the similarity of the extracted features to predefined classes; and
2. an assignment step in which a decision engine 54 assigns class membership. Within this framework, two general methods of classification are proposed. The first uses mutually exclusive classes and therefore assigns each measurement to one class. The second scheme utilizes a fuzzy classification system that allows class membership in more than one class simultaneously. Both methods rely on previously defined classes, as described below.

Class Definition

The development of the classification system requires a data set of exemplar spectral measurements from a representative sampling of the population. Class definition is the assignment of the measurements in the exploratory data set to classes. After class definition, the measurements and class assignments are used to determine the mapping from the features to class assignments.

Class definition is performed through either a supervised or an unsupervised approach. See Y. Pao, *Adaptive Pattern Recognition and Neural Networks*, Addison-Wesley Publishing Co., Reading, Mass. (1989). In the supervised case, classes are defined through known differences in the data. The use of a priori information in this manner is the first step in supervised pattern recognition, which develops classification models when the class assignment is known. For example, the majority of observed spectral variation can be modeled by three abstract factors, which are related to several physical properties including body fat, tissue hydration and skin thickness. Categorizing patients on the basis of these three features produces eight different classes if each feature is assigned a "high" and "low" value. The drawback to this approach is that attention is not given to spectral similarity and the number of classes tends to increase exponentially with the number of features.

Unsupervised methods rely solely on the spectral measurements to explore and develop clusters or natural groupings of the data in feature space. Such an analysis optimizes the within cluster homogeneity and the between cluster separation. Clusters formed from features with physical meaning can be interpreted based on the known underlying phenomenon causing variation in the feature space. However, cluster analysis does not utilize a priori information and can yield inconsistent results.

A combination of the two approaches utilizes a priori knowledge and exploration of the feature space for naturally occurring spectral classes. In this approach, classes are first defined from the features in a supervised manner. Each set of features is divided into two or more regions and classes are defined by combinations of the feature divisions. A cluster analysis is performed on the data and the results of the two approaches are compared. Systematically, the clusters are used to determine groups of classes that can be combined. After conglomeration, the number of final class definitions is significantly reduced according to natural divisions in the data. Subsequent to class definition, a classifier is designed through supervised pattern recognition. A model is created, based on class definitions, that transforms a measured set of features to an estimated classification. Since the ultimate goal of the classifier is to produce robust and accurate calibration models, an iterative approach must be followed in which class definitions are optimized to satisfy the specifications of the measurement system.

Statistical Classification

The statistical classification methods are applied to mutually exclusive classes whose variation can be described statistically. See J. Bezdek, S. Pal, eds, *Fuzzy Models for Pattern Recognition*, IEEE Press, Piscataway, N.J. (1992). Once class definitions have been assigned to a set of exemplary samples, the classifier is designed by determining an optimal mapping or transformation from the feature space to a class estimate which minimizes the number of misclassifications. The form of the mapping varies by method as does the definition of "optimal". Existing methods include linear Discriminant analysis, SIMCA, k nearest-neighbor and various forms of artificial neural networks. See Funkunaga, supra; and Hertz, et al., supra; and Martin, supra; and Duda, et al., supra; and Pao, supra; and S. Wold, M. Sjostrom, SIMCA: A method for analyzing chemical data in terms of similarity and analogy, *Chemometrics: Theory and Application*, ed. B. R. Kowalski, ACS Symposium Series, vol. 52 (1977); and S. Haykin, *Neural Networks: A Comprehensive Foundation*, Prentice-Hall, Upper Saddle River. N.J. (1994). The result is a function or algorithm that maps the feature to a class, c, according to $$c=f(z) \qquad (2)$$

where c is an integer on the interval [1,P] and P is the number of classes. The class is used to select or adapt the calibration model as discussed in the Calibration Section.

Fuzzy Classification

While statistically based class definitions provide a set of classes applicable to blood analyte estimation, the optical properties of the tissue sample resulting in spectral variation change over a continuum of values. Therefore, the natural variation of tissue thickness, hydration levels and body fat content, among others, results in class overlap. Distinct class boundaries do not exist and many measurements are likely to fall between classes and have a statistically equal chance of membership in any of several classes. Therefore, "hard" class boundaries and mutually exclusive membership functions appear contrary to the nature of the target population.

A more versatile method of class assignment is based on fuzzy set theory. See Bezdek, et al., supra; and C. Chen, ed., *Fuzzy Logic and Neural Network Handbook*, IEEE Press, Piscataway, N.J. (1996); and L. Zadeh, Fuzzy Sets, *Inform. Control*, vol. 8, pp. 338–353 (1965). Generally, membership in fuzzy sets is defined by a continuum of grades and a set of membership functions that map the feature space into the interval [0,1] for each class. The assigned membership grade represents the degree of class membership with "1" corresponding to the highest degree. Therefore, a sample can simultaneously be a member of more than one class.

The mapping from feature space to a vector of class memberships is given by $$c_k=f_k(z) \qquad (2)$$

where k=1,2, . . . P, $f_k(\bullet)$ is the membership function of the $k^{th}$ class, $c_k \in [0,1]$ for all k and the vector $c \in \Re^P$ is the set of class memberships. The membership vector provides the degree of membership in each of the predefined classes and is passed to the calibration algorithm.

The design of membership functions utilizes fuzzy class definitions similar to the methods previously described. Fuzzy cluster analysis can be applied and several methods, differing according to structure and optimization approach can be used to develop the fuzzy classifier. All methods attempt to minimize the estimation error of the class membership over a population of samples.

MULTI-TIERED CALIBRATION

Blood analyte prediction occurs by the application of a calibration model to the preprocessed measurement as depicted in FIG. 2. The proposed prediction system involves a calibration or a set of calibration models that are adaptable or selected on the basis of the classification step.

DEVELOPMENT OF LOCALIZED CALIBRATION MODELS

Accurate blood analyte prediction requires calibration models that are capable of compensating for the co-varying interferents, sample heterogeneity, state and structural variations encountered. Complex mixtures of chemically absorbing species that exhibit substantial spectral overlap between the system components are solvable only with the use of multivariate statistical models. However, prediction error increases with increasing variation in interferents that also co-vary with analyte concentration in calibration data. Therefore, blood analyte prediction is best performed on measurements exhibiting smaller interference variations that correlate poorly with analyte concentration in the calibration set data. Since it may not be possible to make all interference variations random, it is desirable to limit the range of spectral interferent variation in general.

The principle behind the multi-tiered classification and calibration system is based on the properties of a generalized class of algorithms that are required to compensate for overlapped interfering signals in the presence of the desired analyte signal. See H. Martens, T. Naes, *Multivariate Calibration*, John Wiley and Sons, New York (1989). The models used in this application require the measurement of multiple independent variables, designated as x, to estimate a single dependent variable, designated as y. For example, y may be tissue glucose concentration, and x may represent a vector, $[x_1\ x_2 \ldots x_i]$, consisting of the noninvasive spectrum signal intensities at each of n wavelengths.

The generalized form of a model to be used in the calculation of a single glucose estimate uses a weighted summation of the noninvasive spectrum as in Equation 4. The weights, w, are referred to as the regression vector.

$$y = \Sigma_{w_i x_i} \quad (4)$$

The weights define the calibration model and must be calculated from a given calibration set of noninvasive spectra in the spectral matrix X, and associated reference values y for each spectrum:

$$w = (X^T X)^{-1} X^T y W. \quad (5)$$

The modeling error that might be expected in a multivariate system using Equation 5 can be estimated using a linear additive mixture model. Linear additive mixtures are characterized by the definition that the sum of the pure spectra of the individual constituents in a mixture equals the spectra of the mixture. Linear mixture models are useful in assessing the general limitations of multivariate models that are based on linear additive systems and those, noninvasive blood analysis, for example, that can be expected to deviate somewhat from linear additive behavior.

Figure 4:
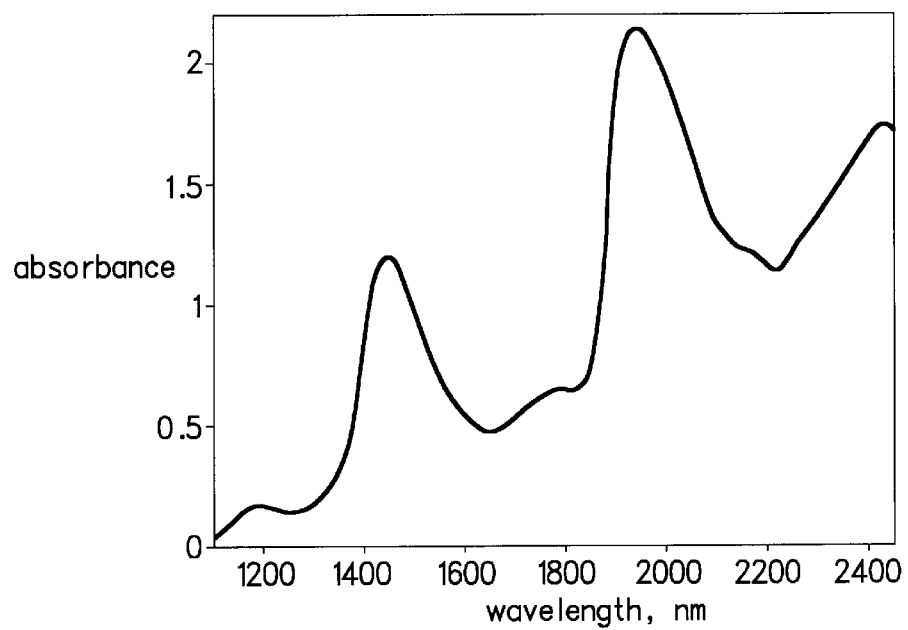
FIG. 4 is a noninvasive absorbance spectrum collected using a diffuse reflectance NIR spectrometer.

FIG. 4 shows an exemplary noninvasive absorbance spectrum. A set of spectral measurements may be represented as a matrix X where each row corresponds to an individual sample spectrum and each column represents the signal magnitude at a single wavelength. The measurement matrix can be represented as a linear additive mixture model with a matrix of instrument baseline variations $B_0$, a matrix of spectra of the pure components K, and the concentrations of the pure components, Y, and random measurement noise present in the measurement of each spectrum, E.

$$X = B_0 + YK^T + E \quad (6)$$

The linear additive model can be broken up further into interferents and analytes as an extended mixture model.

$$X = B_0 + YK^T + TP^T + E \quad (7)$$

In equation 4, T is a matrix representing the concentration or magnitude of interferents in all samples, and P represents the pure spectra of the interfering substances or effects present. Any spectral distortion can be considered an interferent in this formulation. For example, the effects of variable sample scattering and deviations in optical sampling volume must be included as sources of interference in this formulation. The direct calibration for a generalized least squares model on analyte y is $$y_{GLS} = (K^T \Sigma^{-1} K)^{-1} K^T \Sigma^{-1} (x - k_0); \quad (8)$$

where $\Sigma$ is defined as the covariance matrix of the interfering substances or spectral effects, $\sigma$ is defined as the measurement noise, x is the spectral measurement, and $k_0$ is the instrument baseline component present in the spectral measurement.

$$\Sigma = P^T (tt^T)^{-1} P + diag(\delta^2) \quad (9)$$

The derived mean squared error (MSE) of such a generalized least squares predictor is found in Martens, et al., supra.

$$MSE(y_{GLS}) = trace(K^T \Sigma^{-1} K)^{-1} \quad (10)$$

Equation 10 describes the generalized limitations of least squares predictors in the presence of interferents. If K represents the concentrations of blood glucose, a basic interpretation of Equation 10 is: the mean squared error in glucose estimates increases with increasing variation in interferences that also co-vary with glucose concentration in calibration data. Therefore, the accurate estimation of glucose is best performed on measurements exhibiting smaller interference variations that poorly correlate with glucose concentration in the calibration set data. Since it may not be possible to make all interference variations random with glucose, it is desirable to limit the range of spectral interference variation in general. The Multi-Tier Classification provides a method for limiting variation of spectral interferents by placing sample measurements into groups having a high degree of internal consistency. Groups are defined based on a priori knowledge of the sample, instrumental measurements at the tissue measurement site, and extracted features. With each successive tier, samples are further classified such that variation between spectra within a group is successively limited. Tissue parameters to be utilized in class definition may include: stratum corneum hydration, tissue temperature, and dermal thickness.

TISSUE HYDRATION

The stratum corneum (SC), or horny cell layer covers about 10–15 µm thickness of the underside of the arm. The SC is composed mainly of keratinous dead cells, water and some lipids. See D. Bommannan, R. Potts, R. Guy, Examination of the Stratum Comeum Barrier Function In Vivo by Infrared Spectroscopy, *J. Invest. Dermatol.*, vol. 95, pp 403–408 (1990). Hydration of the SC is known to vary over time as a function of room temperature and relative humidity. See J. Middleton, B. Allen, Influence of temperature and humidity on stratum corneum and its relation to skin chapping, *J. Soc. Cosmet. Chem.*, vol. 24, pp. 239–43 (1973). Because it is the first tissue penetrated by the spectrometer incident beam, more photons sample the SC than any other part of the tissue sample. Therefore, the variation of a strong near IR absorber like water in the first layer of the tissue sample can act to change the wavelength and depth intensity profile of the photons penetrating beneath the SC layer.

Figure 5:
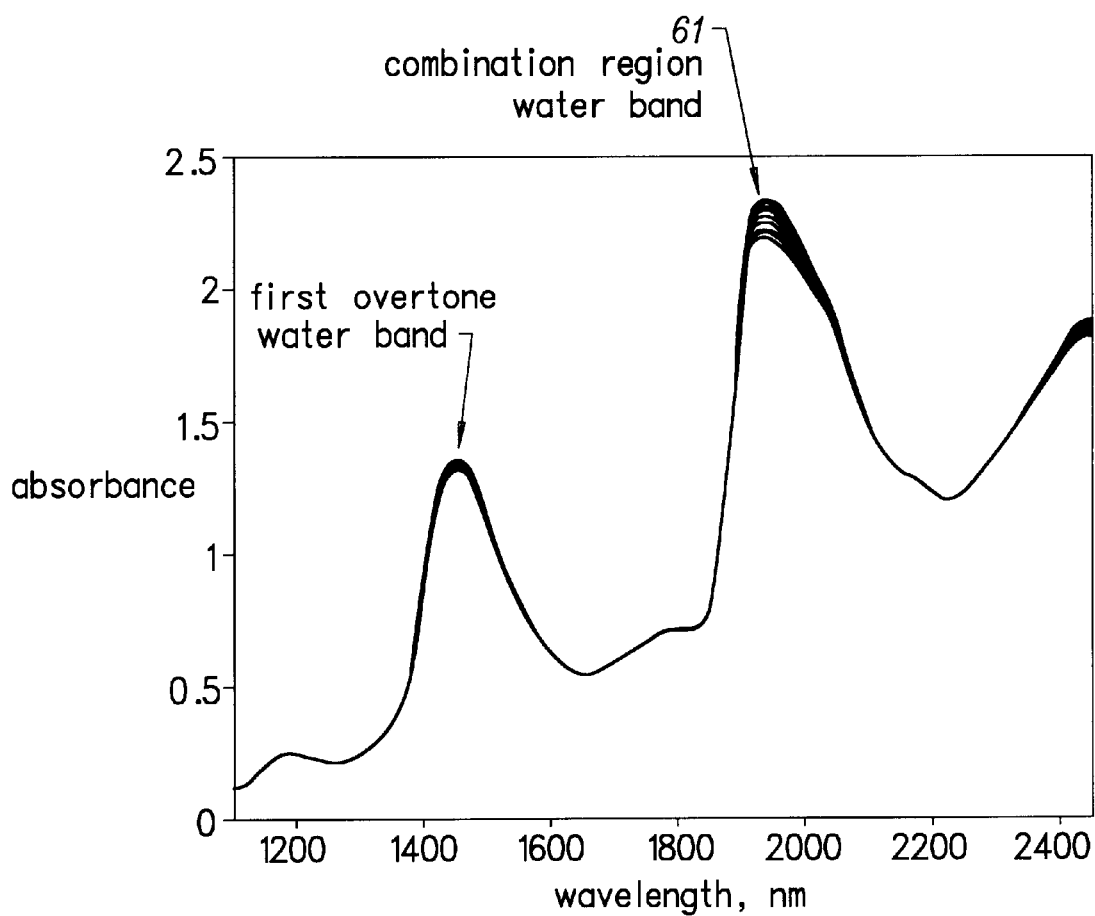
FIG. 5 shows the spectra of repeated noninvasive measurements with no attempt to control tissue hydration.
Figure 6:
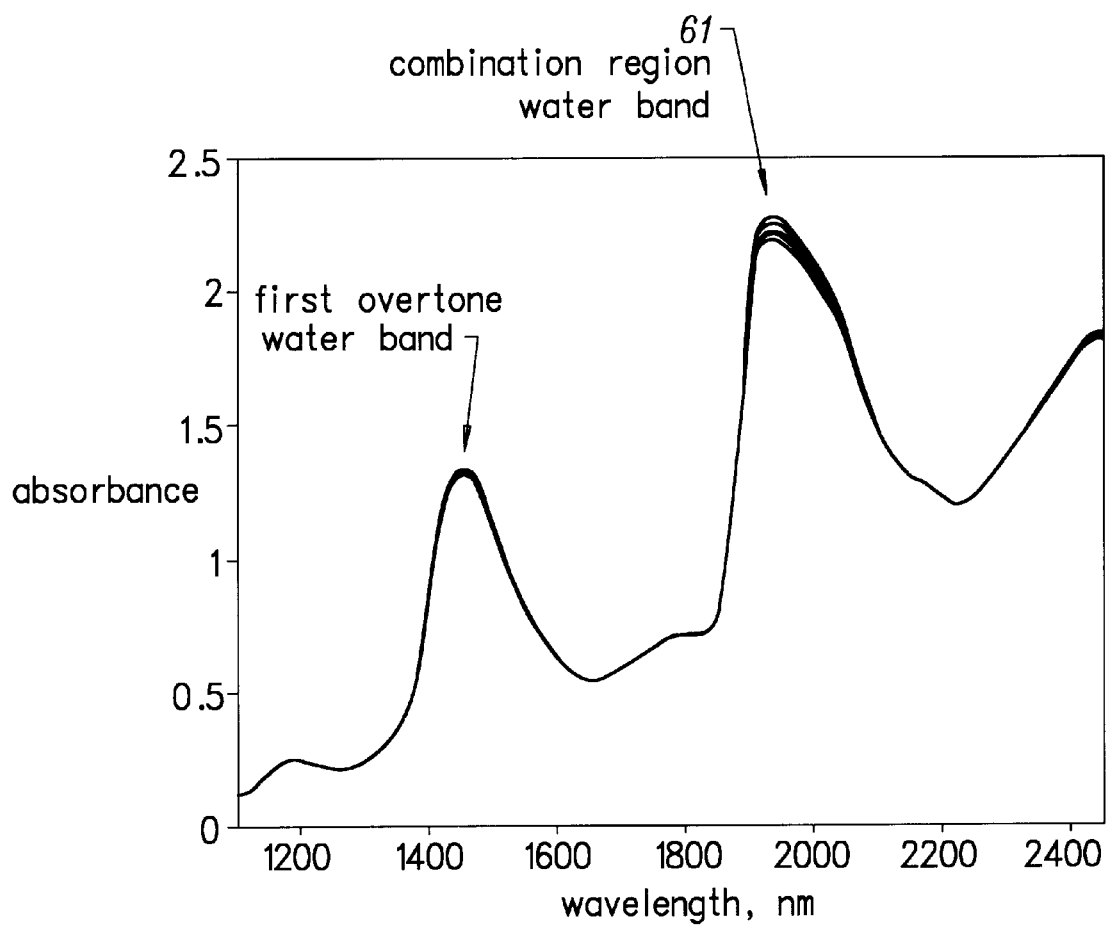
FIG. 6 shows the spectra of repeated noninvasive measurements using ambient humidity to control hydration, according to the invention.

The impact of changes in SC hydration can be observed by a simple experiment. In the first part of the experiment, the SC hydration is allowed to range freely with ambient conditions. In the second part of the experiment, variations in SC hydration are limited by controlling relative humidity to a high level at the skin surface prior to measurement. Noninvasive measurements using uncontrolled and controlled hydration experiments on a single individual are plotted in FIGS. 5 and 6, respectively. Changes in the water band 61 at 1900 nm can be used to assess changing surface hydration. It is apparent that the range of variation in the water band 61 at 1900 nm is considerably narrower in FIG. 6 than in FIG. 5. Since surface hydration represents a large variable in the spectral measurement, it is a valuable component for use in categorizing similarity in tissue samples.

TISSUE TEMPERATURE

The temperature of the measured tissue volume varies from the core body temperature, at the deepest level of penetration, to the skin surface temperature, which is generally related to ambient temperature, location and the amount of clothing at the tissue measurement site. The spectrum of water, which comprises about 65% of living human tissue is the most dominant spectral component at all depths sampled in the 1100–2500 nm wavelength range. These two facts, along with the known temperature-induced shifting of the water band at 1450 nm, combine to substantially complicate the interpretation of information about many blood analytes, including glucose. It is apparent that a range of temperature states exist in the volume of sampled living tissue and that the range and distribution of states in the tissue depend on the skin surface temperature. Furthermore, the index of refraction of skin is known to change with temperature. Skin temperature may therefore be considered an important categorical variable for use in the Multi-Tier Classification to identify groups for the generation of calibration models and prediction.

OPTICAL THICKNESS OF DERMIS

Repeated optical sampling of the tissue is necessary to calibrate to blood constituents. Because blood represents but a part of human tissue, and blood analytes only reside in fractions of the tissue, changes in the optical sampling of tissue may change the magnitude of the analyte signal for unchanging levels of blood analytes. This kind of a sampling effect may confound efforts at calibration by changing the signal strength for specific levels of analyte.

Figure 7:
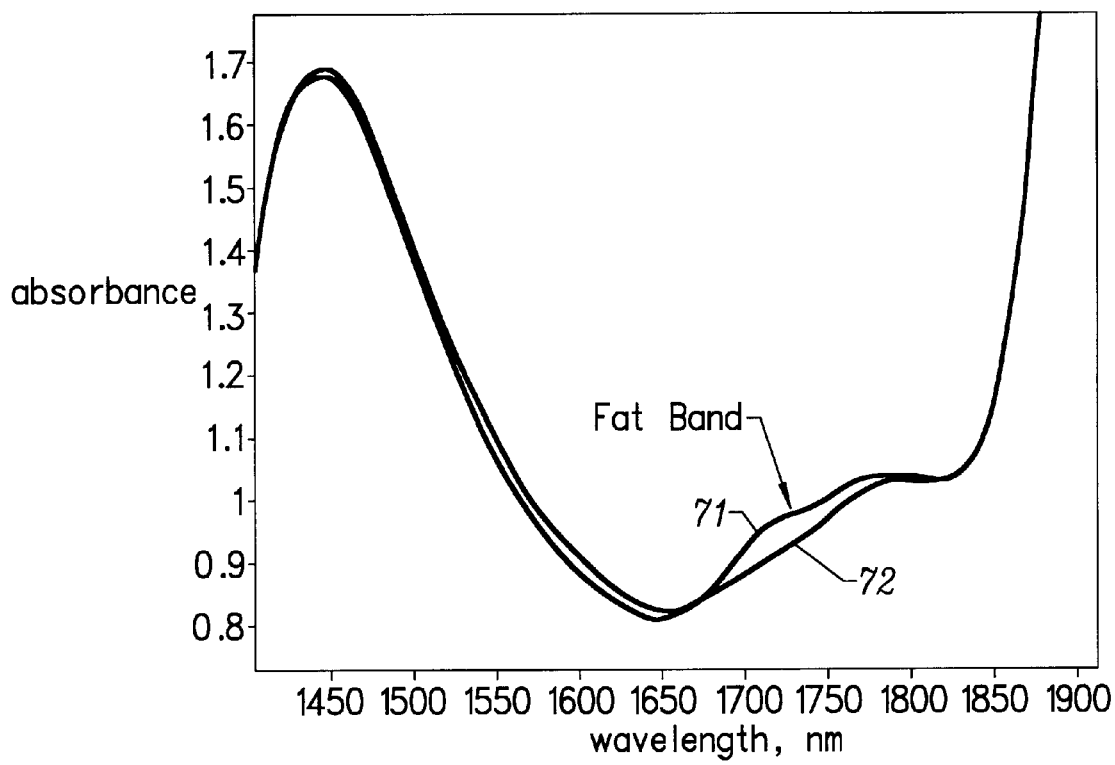
FIG. 7 shows a noninvasive absorbance spectrum having a pronounced fat band at 1710 nm.

Categorization of optical sampling depth is pursued by analyzing spectral marker bands of the different layers. For example, the first tissue layer under the skin is the subcutaneous adipose tissue, consisting mainly of fat. The strength of the fat absorbance band can be used to assess the relative photon flux that has penetrated to the subcutaneous tissue level. A more pronounced fat band means that a greater photon flux has reached the adipose tissue and returned to the detector. In FIG. 7, spectra with pronounced 71 and normal 72 fat bands are presented. The most important use of the optical thickness is to assess the degree of hydration in the interior tissue sampled by the optical probe. Optical thickness may also be a strong function of gender and body type, therefore this property measurement would be useful for assessing interior hydration states within a single individual.

The following sections describe the calibration system for the two types of classifiers, mutually exclusive and fuzzy.

MUTUALLY EXCLUSIVE CLASSES

Figure 8:
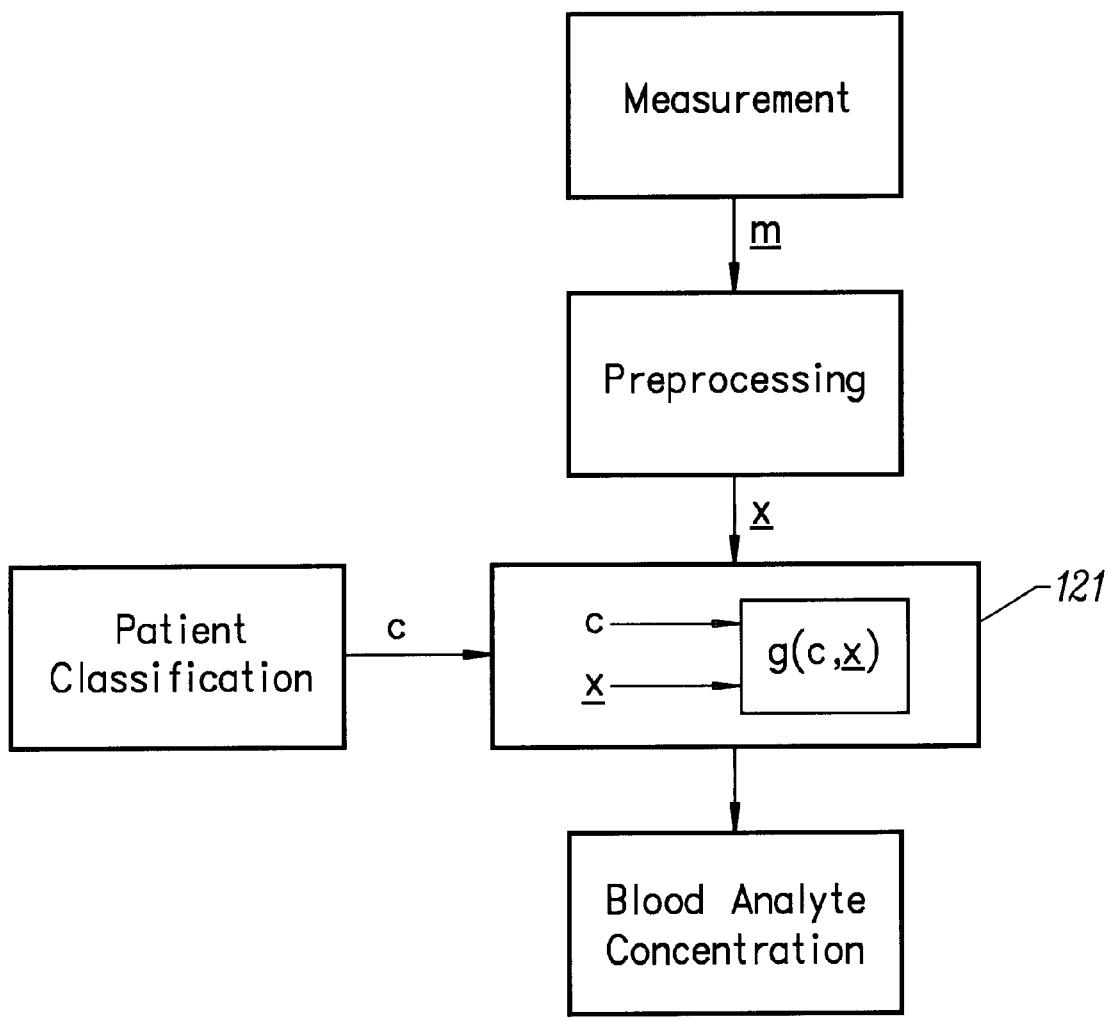
FIG. 8 is a block schematic diagram of a general calibration system for mutually exclusive classes, according to the invention.

In the general case, the designated classification is passed to a nonlinear model that provides a blood analyte prediction based on the patient classification and spectral measurement. This process, illustrated in FIG. 8, involves the modification of the estimation strategy for the current subject according to the structural tissue properties and physiological state manifested in the absorbance spectrum.

This general architecture necessitates a nonlinear calibration model 101 such as nonlinear partial least squares or artificial neural networks since the mapping is highly nonlinear. The blood analyte prediction for the preprocessed measurement x with classification specified by c is given by $$\hat{y}=g(c,x) \tag{11}$$

where g(•) is a nonlinear calibration model which maps x and c to an estimate of the blood analyte concentration, $\hat{y}$.

In the preferred realization, a different calibration is realized for each class. The estimated class is used to select one of p calibration models most appropriate for blood analyte prediction using the current measurement. Given that k is the class estimate for the measurement, the blood analyte prediction is $$\hat{y}=g_k(x), \tag{12}$$

where $g_k(\bullet)$ is the calibration model associated with the $k^{th}$ class.

The calibrations are developed from a set of exemplar absorbance spectra with reference blood analyte values and pre-assigned classification definitions. This set, denoted the "calibration set", must have sufficient samples to completely represent the range of physiological states to be encountered in the patient population. The p different calibration models are developed individually from the measurements assigned to each of the p classes. The models are realized using known methods including principal component regression, partial least squares regression and artificial neural networks. See Hertz, et al., supra; and Pao, supra; and Haykin, supra; and Martens, et al., supra; and N. Draper, H. Smith, *Applied Regression Analysis*, $2^{nd}$ ed., John Wiley and Sons, New York (1981). The various models associated with each class are evaluated on the basis of an independent test set or cross validation and the "best" set of models are incorporated into the Multi-tier Classification. Each class of patients then has a calibration model specific to that class.

FUZZY CLASS MEMBERSHIP

Figure 9:
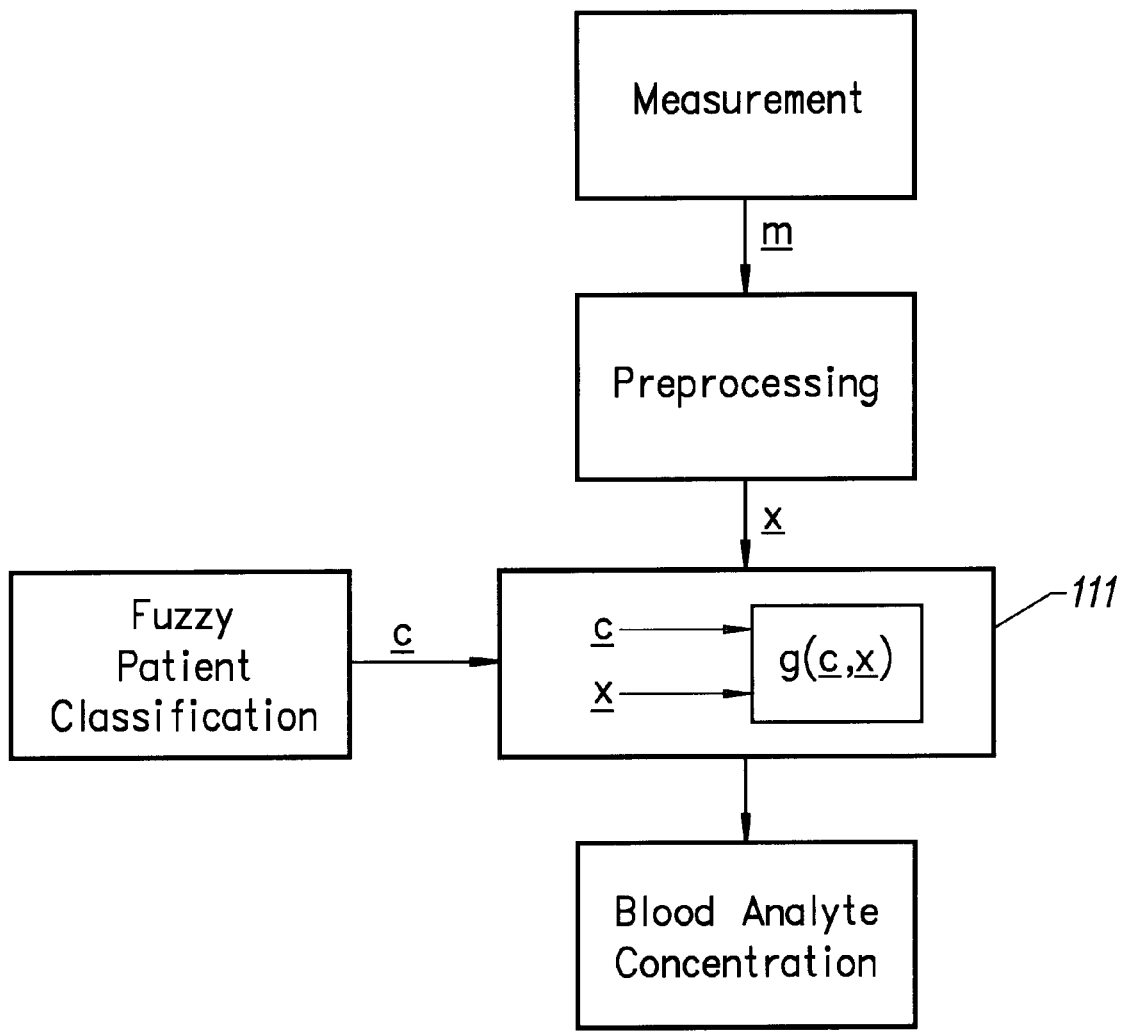
FIG. 9 is a block schematic diagram of a general calibration system for fuzzy class assignments, according to the invention.

When fuzzy classification is employed the calibration is passed a vector of memberships rather than a single estimated class. The vector, c, is utilized to determine an adaptation of the calibration model suitable for blood analyte prediction or an optimal combination of several blood analyte predictions. In the general case, illustrated in FIG. 9, the membership vector and the preprocessed absorbance spectrum are both used by a single calibration 111 for blood analyte prediction. The calculation is given by $$\hat{y}=g(c,x) \tag{13}$$

where $g(\bullet)$ is a nonlinear mapping determined through nonlinear regression, nonlinear partial least squares or artificial neural networks. The mapping is developed from the calibration set described previously and is generally complex.

Figure 10:
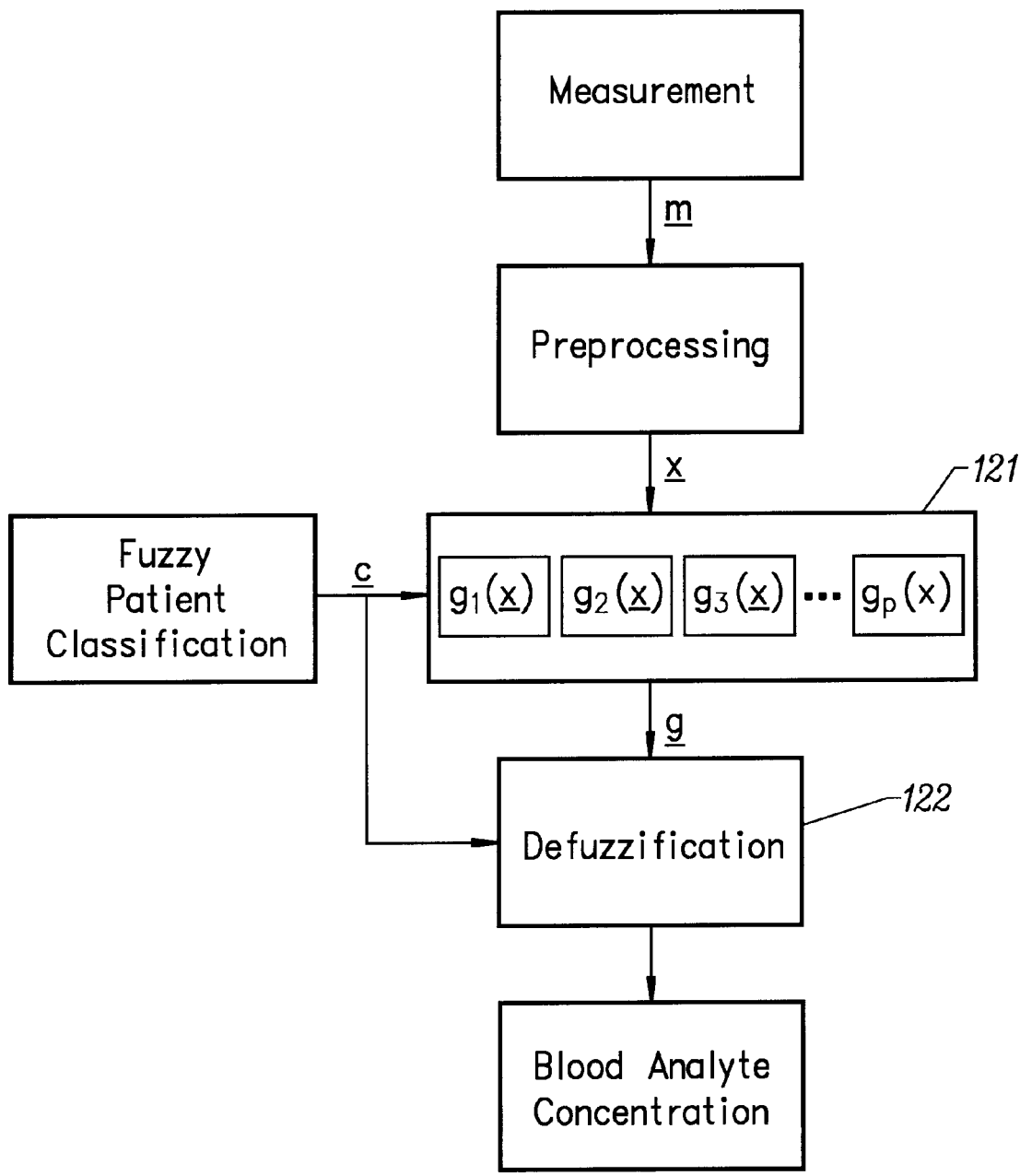
FIG. 10 is a block schematic diagram showing an example of parallel calibration models for fuzzy set assignments, according to the invention.

The preferred realization, shown in FIG. 10, has separate calibrations 121 for each class. However, each calibration is generated using all measurements in the calibration set by exploiting the membership vector assigned to each measurement. In addition, the membership vector is used to determine an optimal combination of the p blood analyte predictions from all classes through defuzzification 122. Therefore, during calibration development, a given measurement of the calibration set has the opportunity to impact more than one calibration model. Similarly, during prediction more than one calibration model is used to generate the blood analyte estimate.

Each of the p calibration models is developed using the entire set of calibration data. However, when the $k^{th}$ calibration model is calculated, the calibration measurements are weighted by their respective membership in the $k^{th}$ class. As a result, the influence of a sample on the calibration model of a particular class is a function of its membership in the class.

In the linear case, weighted least squares is applied to calculate regression coefficients and, in the case of factor based methods, the covariance matrix. See Duda, et al., supra. Given a matrix of absorbance spectra $X_k \in \Re^{r \times w}$ and reference blood analyte concentrations $Y \in \Re^r$ where r is the number of measurement spectra and w is the number wavelengths, let the membership in class k of each absorbance spectrum be the elements of $C_k \in \Re^r$. Then the principal components are given by $$F=X_k M, \tag{14}$$

where M is the matrix of the first n eigenvectors of P. The weighted covariance matrix P is determined through $$P=X_k V X_k^T, \tag{15}$$

where V is a square matrix with the elements of $C_k$ on the diagonal. The regression matrix, B, is determined through $$B=(F^T V F)^{-1} F^T V Y. \tag{16}$$

When an iterative method is applied, such as artificial neural networks, the membership is used to determine the frequency the samples are presented to the learning algorithm. Alternatively, an extended Kalman filter is applied with a covariance matrix scaled according to V.

The purpose of defuzzification is to find an optimal combination of the p different blood analyte predictions, based on a measurement's membership vector that produces accurate blood analyte predictions. Therefore, defuzzification is a mapping from the vector of blood analyte predictions and the vector of class memberships to a single analyte prediction. The defuzzifier can be denoted as transformation such that $$\hat{y}=d(c,[y_1 y_2 y_3 \ldots y_P]), \tag{17}$$

where $d(\bullet)$ is the defuzzification function, c is the class membership vector and $y_k$ is the blood analyte prediction of the $k^{th}$ calibration model. Existing methods of defuzzification, such as the centroid or weighted average, are applied for small calibration sets. However, if the number of samples is sufficient, $d(\bullet)$ is generated through a constrained nonlinear model.

INSTRUMENT DESCRIPTION

The Multi-tiered Classification and Calibration is implemented in a scanning spectrometer which determines the NIR absorbance spectrum of the subject forearm through a diffuse reflectance measurement. The instrument employs a quartz halogen lamp, a monochromator, and InGaAs detectors. The detected intensity from the sample is converted to a voltage through analog electronics and digitized through a 16-bit A/D converter. The spectrum is passed to the Intelligent Measuring System (IMS) for processing and results in either a glucose prediction or a message indicating an invalid scan.

Although the invention is described herein with reference to the preferred embodiment, one skilled in the art will readily appreciate that other applications may be substituted for those set forth herein without departing from the spirit and scope of the present invention. Accordingly, the invention should only be limited by the claims included below.

What is claimed is:

1. A method of developing a multi-tiered calibration model for estimating concentration of a target blood analyte from measured tissue spectra, comprising the steps of:

providing a calibration set, wherein said calibration set comprises a data set of exemplar spectral measurements from a representative sampling of a subject population;

initially, classifying said exemplar measurements into previously defined classes based on a priori information pertaining to a corresponding subject;

further classifying said exemplar measurements into previously defined classes based on at least one instrumental measurement at a tissue measurement site;

extracting at least one feature from said exemplar measurements for still further classification, wherein a decision rule makes class assignments; and calculating at least one localized calibration model based on said classified measurements and an associated set of reference values.

2. The method of claim 1, wherein said initial classification step comprises the steps of:

in a first tier, classifying said measured spectrum into previously defined classes based on subject's age; and in a second tier, further classifying said measured spectrum into previously defined classes based on subject's sex.

3. The method of claim 1, wherein said further classification step further comprises the steps of:

in a third tier further classifying said exemplar measurements into previously defined classes based on an estimation of stratum corneum hydration at said tissue measurement site; and in a fourth tier, further classifying said exemplar measurements into previously defined classes based on skin temperature at said tissue measurement site.

4. The method of claim 3, wherein said stratum corneum hydration estimate is based on a measurement of ambient humidity at said tissue measurement site.

5. The method of claim 1, wherein said feature extraction step comprises any mathematical transformation that enhances a quality or aspect of sample measurement for interpretation to represent concisely structural properties and physiological state of a tissue measurement site, wherein a resulting set of features is used to classify a subject and determine a calibration model that is most useful for blood analyte prediction.

6. The method of claim 5, wherein said features are represented in a vector, $z\Sigma\Re^M$ that is determined from a preprocessed measurement through:

$$z=f(\lambda,x)$$

where $f(\bullet): \Re^N \to \Re^M$ is a mapping from a measurement space to a feature space, wherein decomposing $f(\bullet)$ yields specific transformations, $f_i(\bullet): \Re^N \to \Re^M_i$, for determining a specific feature, wherein the dimension $M_i$ indicates whether an $i^{th}$ feature is a scalar or a vector and an aggregation of all features is the vector z, and wherein a feature exhibits a certain structure indicative of an underlying physical phenomenon when said feature is represented as a vector or a pattern.

7. The method of claim 6, wherein individual features are divided into categories, said categories comprising:
   abstract features that do not necessarily have a specific interpretation related to a physical system; and
   simple features that are derived from an a priori understanding of a sample and that can be related directly to a physical phenomenon.

8. The method of claim 7, wherein said simple features can be calculated from NIR spectral absorbance measurements, said simple features including any of:
   thickness of adipose tissue;
   hematocrit level;
   tissue hydration;
   magnitude of protein absorbance;
   scattering properties of said tissue;
   skin thickness;
   temperature related effects;
   age related effects;
   spectral characteristics;
   pathlength estimates;
   volume fraction of blood in tissue; and
   spectral characteristics related to environmental influences.

9. The method of claim 1, further comprising the step of: employing spectral decomposition to determine features related to a known spectral absorbance pattern.

10. The method of claim 1, further comprising the step of:
   employing factor-based methods to build a model capable of representing variation in a measured absorbance spectrum related to a demographic variable;
   wherein projection of a measured absorption onto said model constitutes a feature that represents spectral variation related to said demographic variable.

11. The method of claim 1, wherein said feature extraction step assigns a measurement to one of many predefined classes.

12. The method of claim 1, further comprising the steps of;
   measuring the similarity of a feature to predefined classes; and
   assigning class membership.

13. The method of claim 1, further comprising the step of;
   using measurements and class assignments to determine a mapping from features to class assignments.

14. The method of claim 13, further comprising the steps of:
   defining classes from said features in a supervised manner, wherein each set of features is divided into two or more regions, and wherein classes are defined by combination of feature divisions;
   performing a cluster analysis on the spectral data to determine groups of said defined classes that can be combined, wherein the final number of class definitions is significantly reduced;
   designing a classifier subsequent to class definition through supervised pattern recognition by determining an optimal mapping or transformation from the feature space to a class estimate that minimizes the number of misclassifications; and
   creating a model based on class definitions that transforms a measured set of features to an estimated classification, wherein said class definitions are optimized to satisfy specifications of a measurement system used to take said measurements.

15. The method of claim 14, wherein said optimized classes comprise groups of measurements wherein similarity between measurements within a group is greater than similarity between groups.

16. The method of claim 15, said step of calculating at least one localized calibration model comprising:
   calculating weights, w, for said exemplar measurements according to:

$$W=(X^TX)^{-1}X^Ty,$$

where X represents a matrix of spectral measurements, and y represents a reference value of said target analyte concentration for each measurement.

17. The method of claim 16, wherein a vector of weights of spectral measurements within one of said groups comprises a regression vector for said group;
   wherein said regression vector comprises a calibration model for said group.

18. A method of developing a multi-tiered calibration model for estimating concentration of a target blood analyte from measured tissue spectra, comprising the steps of:
   providing a calibration set, wherein said calibration set comprises a data set of exemplar spectral measurements from a representative sampling of a subject population;
   in at least one tier, classifying said exemplar measurements into previously defined classes; and
   extracting at least one feature from said exemplar measurements for still further classification; and
   calculating at least one localized calibration model based on said classified exemplar measurements and a set of associated reference values.

19. The method of claim 18, wherein said classifying step is based on any of:
   abstract and simple features.

20. The method of claim 18, further comprising the step of mapping said exemplar measurements to estimates of said analyte based on either a linear or a nonlinear model.

21. The method of claim 18, wherein said classifying step is based on any of:
   a priori information; and
   at least one instrumental measurement at a tissue measurement site at which optical samples were taken for said spectral measurements.

22. The method of claim 18, wherein said classifying step comprises multiple tiers.

23. The pattern classification method of claim 22, wherein said classifying step comprises any of the steps of:
   classifying said exemplar measurements into previously defined classes based on subject's age;

classifying said exemplar measurements into previously defined classes based on subject's sex;

classifying said exemplar measurements into previously defined classes based on an estimation of stratum corneum hydration at said tissue measurement site; and classifying said exemplar measurements into previously defined classes based on skin temperature at said tissue measurement site.

* * * * *